(12) United States Patent
Kincaid et al.

(10) Patent No.: US 7,015,782 B2
(45) Date of Patent: Mar. 21, 2006

(54) MAGNETO-MECHANICAL APPARATUS

(75) Inventors: Stephen Kincaid, Gilbert, AZ (US);
George M. Acosta, Phoenix, AZ (US);
Roxanne Abul-Haj, Mesa, AZ (US);
Kevin H. Hazen, Gilbert, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 0 days.

(21) Appl. No.: 10/752,369

(22) Filed: Jan. 5, 2004

(65) Prior Publication Data

US 2004/0239461 A1 Dec. 2, 2004

Related U.S. Application Data

(63) Continuation-in-part of application No. 10/472,856, filed on Sep. 18, 2003.

(60) Provisional application No. 60/500,382, filed on Sep. 5, 2003, provisional application No. 60/448,840, filed on Feb. 19, 2003.

(51) Int. Cl.
*H01F 7/20* (2006.01)
*H01H 9/00* (2006.01)

(52) U.S. Cl. ............... 335/306; 335/205; 335/207
(58) Field of Classification Search ........ 335/205–207, 335/285, 302–306; 310/90.5
See application file for complete search history.

(56) References Cited

U.S. PATENT DOCUMENTS 4,674,338 A * 6/1987 Carpenter ............... 73/861.77
5,877,664 A * 3/1999 Jackson, Jr. ............... 335/205

* cited by examiner

*Primary Examiner*—Ramon M. Barrera
(74) *Attorney, Agent, or Firm*—Michael A. Glenn; Glenn Patent Group

(57) ABSTRACT

A magnetic field based mechanical apparatus is disclosed. The apparatus is based on coupled attracting or opposing magnets in conjunction with the insertion or removal of a magnetic field modifier. In the preferred embodiment, two repelling magnets are drawn together with the insertion of a magnetic field modifier. The field modifier may be another magnet having an opposing pole. Removal of the field modifier returns the forces to their original states. This oscillating motion may be driven with a low energy and/or small power supply. The resulting motion of the opposing magnets can drive mechanical system such as a linear, gear, ratchet, or reciprocating drive.

61 Claims, 7 Drawing Sheets

MAGNETO-MECHANICAL APPARATUS

CROSS-REFERENCE TO RELATED APPLICATIONS

This application is a Continuation-in-Part of the U.S. patent application Ser. No. 10/472,856 filed on 18 Sep. 2003 and claims priority to the U.S. Provisional Patent Application Ser. No. 60/500,382 filed on 5 Sep. 2003, and is related to U.S. Pat. No. 6,152,876, U.S. Pat. No. 6,040,578, and U.S. Provisional Patent Application 60/448,840 filed on 19 Feb. 2003, the contents of all of which are incorporated by reference herein by the reference thereto.

BACKGROUND OF THE INVENTION

1. The Field of the Invention

This invention generally relates to magneto-mechanical devices. More particularly, the invention relates to a magneto-mechanical apparatus with a magnetic field modifier that, when inserted into or removed from the magnetic field between two magnet components of the apparatus, triggers a displacement of at least one of the magnet components, which is coupled to a drive or a switch.

2. Description of the Related Arts

There exist a large number of types of mechanical drives. However, there exist far fewer drives based upon a magnetic field, the most relevant of which are reviewed here.

U.S. Pat. No. 4,304,532 discloses a pump system, which has a magnetic drive including a rotatable driver component and a driven component provided with blades for imparting motion to a fluid and mounted on a stationary shaft forming a one-piece unit with a thin diaphragm positioned between the driver component and the driven component. The driver component and the driven component include a plurality of permanent magnets. Each magnet has a central aperture dimensioned so that the attracting force is equal throughout the body of the magnet.

U.S. Pat. No. 5,494,415 discloses a magnetically driven pump for transferring fluid through a conduit. The pump includes an electromagnet assembly selectively excited by a power source and a non-ferromagnetic lever structure extending from the electromagnet assembly to the conduit. The lever structure has a ferro-magnetic portion, which may consist of a plate, at one end movable by the electromagnet assembly between a release position where the ferro-magnetic portion is angularly offset relative to the electromagnet assembly and a compression position where the ferromagnetic portion is in parallel contact with the electromagnet assembly. The ferro-magnetic portion enables a striker portion at another end of the lever structure to compress the conduit at a predetermined frequency. The lever structure couples movement of the ferro-magnetic portion at one end with movement of a striker at the other end such that the ferro-magnetic portion moves within a lesser arcuate range and the striker moves within a greater arcuate range. To reduce operating noise, the lever may be pivotally mounted on a translating shaft, enabling a part of the ferro-magnetic portion to remain in contact with the electromagnet assembly while in and between the release and compression positions.

U.S. Pat. No. 4,850,821 and European Patent EP0282095 disclose a multiple magnet drive pump. The magnetic drive pump includes a driving magnet that has opposite polarities circumferentially spaced apart from each other, a plurality of driven magnets on a circumference of the driving magnet for rotation in a non-contact state therewith, and a plurality of pump sections each having the driven magnet incorporated into a rotor for a pumping operation.

European Patent EP0291780 discloses a pump, which includes a body having two parts forming a tight assembly, two apertures for the admission and outlet of a liquid to be pumped and means of connection to allow pipes to be connected in the vicinity of these apertures, and a rotary device such as a screw, fixed inside the body, to draw the liquid in through one aperture and deliver it through the other. The two assembled parts of the body and the rotating device are made of a ceramic, composed mainly of aluminum, zirconium oxide, silicon nitride, or silicon carbide. Such a pump may be made without any joint and convey virtually any type of liquid at either high or low temperature.

None of these patents teaches a magnetic field modifier used to drive a switch and/or a mechanical drive.

It is observed that for both mechanical and magneto-mechanical based drives, a further reduction of the power requirements of the drives and/or the physical dimensions of the drives is desirable.

SUMMARY OF THE INVENTION

A magnetic field based mechanical apparatus is disclosed. The apparatus is based on coupled attracting or opposing magnets in conjunction with the insertion and/or removal of a magnetic field modifier. The movement of the magnetic field modifier results in a displacement of at least one of the coupled magnets relative to the other coupled magnet. The at least one of the coupled magnets is mechanically associated with a drive and/or a switch.

In the preferred embodiment, two repelling magnets are drawn together with the insertion of a magnetic field modifier. The field modifier may be a piece of magnetizable metal or another magnet with an opposing pole. Removal of the field modifier returns the magnets to their original states. The energy required for introducing the magnetic field modifier between the coupled magnets, which results in the motion of at least one of the coupled magnets, is less than the direct force required to move the coupled magnets in the same fashion. The oscillating motion may be driven with a low energy and/or small power supply. The resulting motion of the opposing magnets can be linked to a switch or a mechanical system such as a linear, gear, ratchet, or reciprocating drive.

One benefit of the apparatus is the reduction of the energy necessary to induce relative movement of the coupled magnets. Another benefit is the reduction of the spatial constraints for coupling to a drive mechanism. Another benefit is that the invention can be utilized in a large range of gear or pump driven systems.

DETAILED DESCRIPTION OF THE PREFERRED EMBODIMENTS

Figure 1:
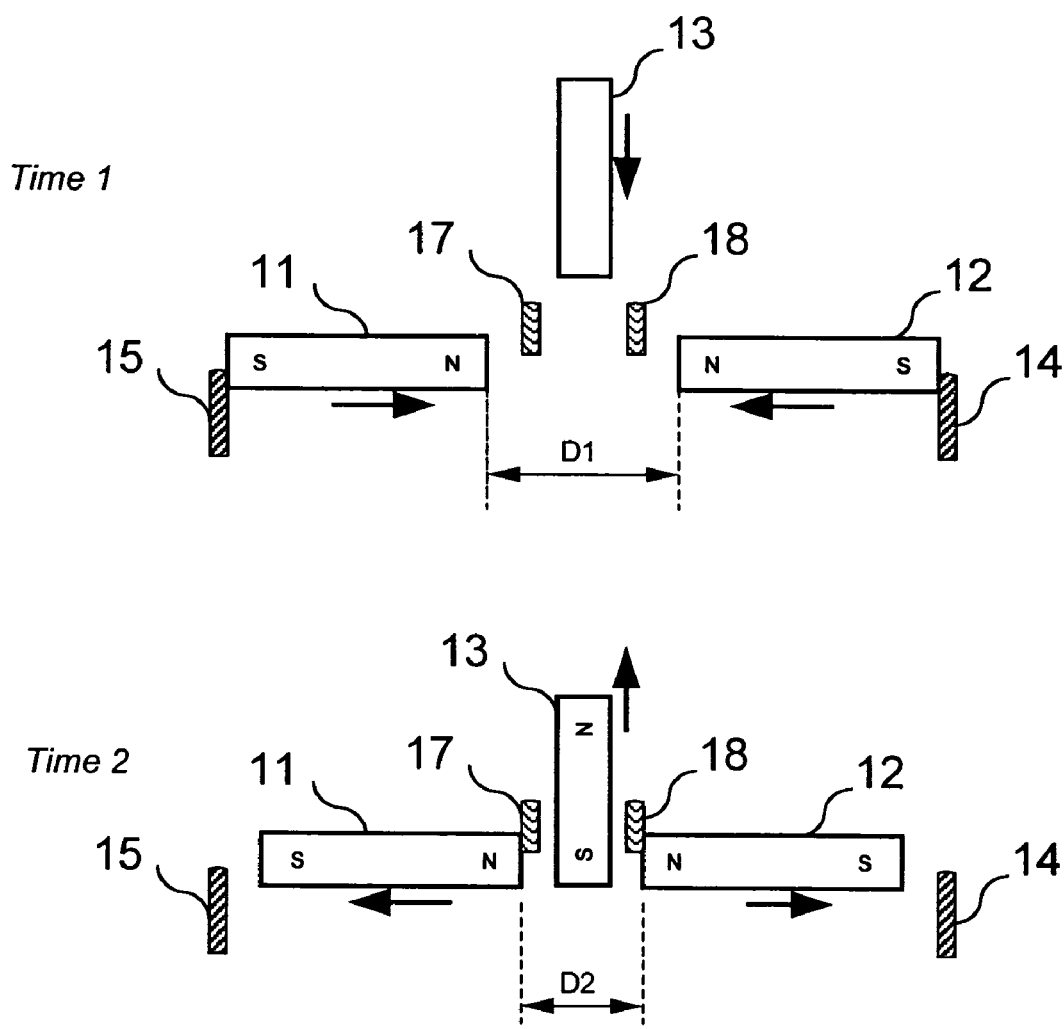
FIG. 1 is a schematic diagram illustrating a magnetic switch triggered by a magnetic filed modifier according to one embodiment of the invention.

Referring to the drawings, in particular to FIG. 1 wherein a magnetic switch according to the first preferred embodiment of the invention is illustrated. The switch includes two coupled magnets 11 and 12 that are aligned with the like poles facing to each other resulting in a repelling force driving the coupled magnets apart. In this embodiment, the magnets 11 and 12 repel each other until they reach a dynamic equilibrium supported by the optional mechanical stops 14 and 15 as illustrated in the state of time 1 in FIG. 1. The magnets 11 and 12 may be pushed toward one another by applying an external force along the length of the magnets toward the center point between the magnets.

For the purpose of this invention, a third member 13 is inserted between the coupled magnets 11 and 12 as a magnetic field modifier to alter the repelling force between the magnets into two attracting forces. The magnetic field modifier 13 in the illustrated example is a magnetizable metal sheet or a metal bar, which is either not-yet-magnetized or already-magnetized. When a not-yet-magnetized piece of metal is pushed or pulled with a force that places at least the tip of the metal into the repulsive magnetic field between the coupled magnets 11 and 12, the not-yet-magnetized metal magnetizes within the field to a pole opposite that of the nearest ends of the coupled magnets 11 and 12. The result of this operation is that the original repulsive magnetic field between the coupled magnets 11 and 12 is replaced by two attractive magnetic fields: one between the magnet 11 and the magnetic field modifier 13, and the other between the modifier 13 and the magnet 12. When the magnetic field modifier 13 reaches a critical position, the attractive forces overcome the original repelling force and the coupled magnets 11 and 12 are drawn toward each other as shown in the state of time 2 in FIG. 1.

In the illustrated example, the coupled magnets 11 and 12 draw together until they reach the optional mechanical stops 17 and 18. The insertion of the magnetic field modifier 13 changes the distance from D1 to D2 and thus results in a switch being thrown. Such a switch can be used in many ways either mechanically or electrically. Notably, the force required to insert the magnetic field modifier 13 and throw the switch is less than the force required to move the coupled magnets 11 and 12 to the same location without the use of the magnetic field modifier 13. In other words, the power required to break the field is less than that required for a direct mechanical drive.

The mechanical stops 17 and 18 should be placed in such a manner that they may not interfere with the magnetic field between the coupled magnets 11 and 12. Preferably, the mechanical stops 17 and 18 are placed adjacent to the outer edge of the coupled magnets 11 and 12 so that the magnetic field impact of the mechanical stops relative to the magnetic field modifier 13 minimized.

Optionally, the moving path of the coupled magnets 11 and 12 may be limited by one or more guides.

Those skilled in the art will readily understand that a large number of configurations of the invention illustrated in FIG. 1 may be alternatively used without fundamental changes. For example, the magnetic fields illustrated in FIG. 1 may be reversed. The coupled magnets in FIG. 1 are pictured with the north poles facing each other, which result in the inserted magnetic field modifier 13 having a south pole being induced. Alternatively, the coupled magnets may have the south poles facing each another, which would result in the inserted magnetic field modifier 13 having a north pole being induced. For another example, the inserted magnetic field modifier 13 may be a magnet itself. In this case, the inserted pole will have the opposite alignment of the poles facing one another in the coupled magnets.

Additional parameters may be varied such as the size of the magnets, the relative alignment of the coupled magnets to the field modifier, the distance between the magnets, the existence and placement of stops, guides for controlling the coupled magnets or field modifier movement, and the throw distance between the magnets. The coupled magnets need not be directly on a line as pictured. Similarly, the magnetic field modifier does not need to enter the magnetic field between the coupled magnets at a ninety degree angle. It is preferable that permanent magnets are used for the coupled magnets due to power consumption. Electromagnets can be used, but they require more power.

The switch illustrated in FIG. 1 can be reversibly used, i.e. the pre-inserted magnetic field modifier 13 may be removed to create a repelling force between the coupled magnets 11 and 12. When the departing magnetic field modifier 13 reaches a critical position, the repelling force between the coupled magnets 11 and 12 becomes larger than the two attractive magnetic fields, and the coupled magnets 11 and 12 move apart. Thus, the initial configuration is reached. In this case, the magnets move apart until optional mechanical stops 14 and 15 are reached. The cycle of inserting and removing the magnetic field modifier 13 may be repeated. The opposing forces of the attraction to the magnetic field modifier 13 and the repulsion of the coupled magnets 11 and 12 vary with the position of the magnetic field modifier 13.

A small displacement about the balance position of these opposing forces could drive the coupled magnets 11 and 12 one way or the other. Thus, the throw space required for the magnetic field modifier 13 is small and the apparatus used to induce the throw may also be small.

It will be readily apparent to those skilled in the art that a number of mechanisms exist that could move the magnetic field modifier 13. For example, mechanical, pressurized, or electrical systems may be used to move the magnetic field modifier 13. In addition, the magnetic field modifier 13 may be in any shape. For example, it can be a metal bar or a metal sheet as in the example illustrated in FIG. 1. It can also be a chopper wheel that spins between the coupled magnets 11 and 12. Different sections of the wheel would alternately result in attractive or repelling forces between the opposing coupled magnets 11 and 12. Additional accessories such as counters may be readily coupled to such a mechanism.

The repeating relative motion of opposing field coupled magnets 11 and 12 may be mechanically coupled to a drive system. Examples of this coupling are described below.

Figure 2:
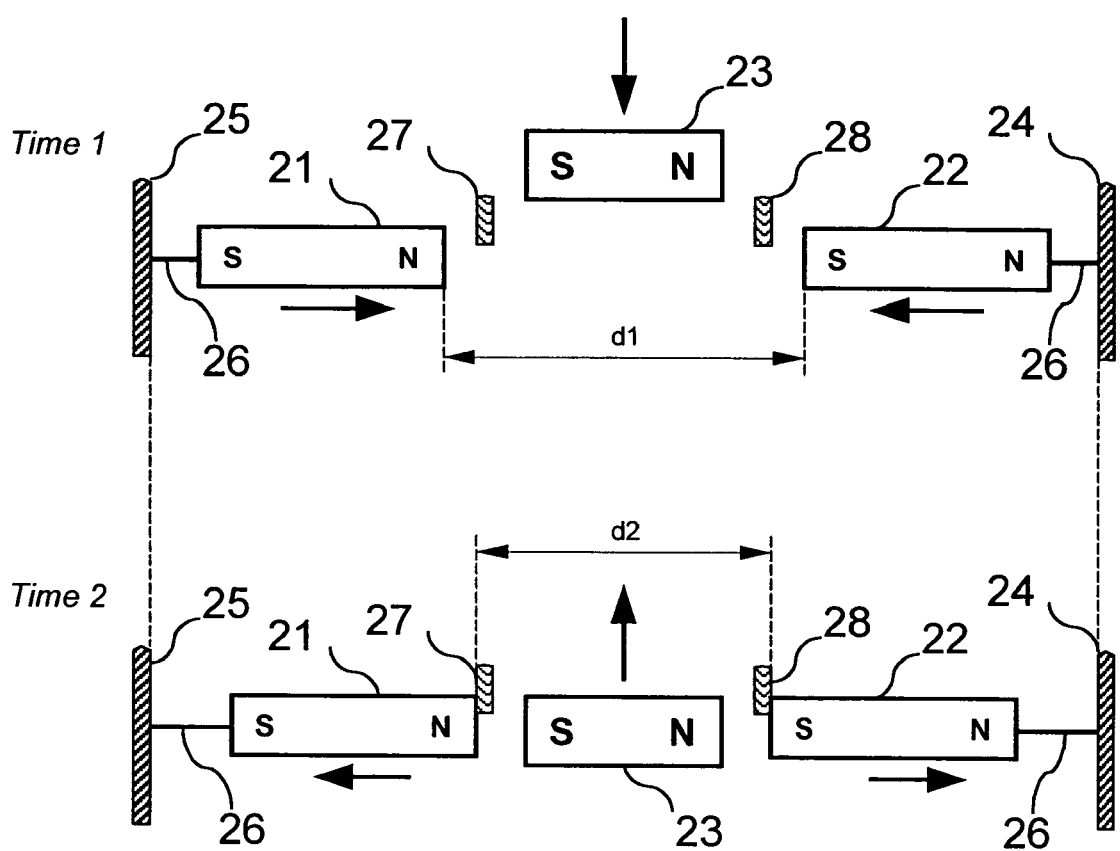
FIG. 2 is a schematic diagram illustrating a magnetic switch triggered by a magnetic filed modifier according to another embodiment of the invention.

FIG. 2 is a schematic diagram illustrating a magnetic switch with coupled magnets 21 and 22 of opposite polarity according to the second preferred embodiment of the invention. In this embodiment, the coupled magnets 21 and 22 are aligned with unlike or opposite poles facing each other. An attractive force is used to draw the coupled magnets 21 and 22 toward each other. An opposing force 26 is applied to maintain an initial distance between the two magnets 21 and 22 as illustrated in the state of time 1 in FIG. 2. The opposing force 26 may be provided by a mechanical device such as a spring. The inserted magnetic field modifier 23 strengthens the attractive force between the magnets 21 and 22 as illustrated in the state of time 2 in FIG. 2. The resulting additional attractive forces pull the coupled magnets 21 and 22 further toward each other. This causes the change of distance between the magnets from d1 to d2. In this case, the attraction brings the coupled magnets 11 and 12 toward each other until the mechanical stops 27 and 28 are reached.

As in the example of FIG. 1, the insertion and removal of the magnetic field modifier is reversible, requires lower amounts of energy than applying direct forces, and may be performed under different steric constraints, including a smaller space requirement. As in the example of FIG. 1, the configuration of the magnets may be reversed though different optional mechanical guides and/or stops would then be used. Like in the example of FIG. 1, those skilled in the art will be ready to recognize the large variety of arrangements and parameters that may be used without deviating from the same general invention concept illustrated in the example of FIG. 2. Again, the repeating relative motion of attractive field coupled magnets may be mechanically coupled to a drive system.

The mechanical stops 27 and 28 should be placed in such a manner that they may not interfere with the magnetic field between the coupled magnets 21 and 22. Preferably, the mechanical stops 27 and 28 are placed adjacent to the outer edge of the coupled magnets 21 and 22 so that the magnetic field impact of the mechanical stops relative to the magnetic field modifier 23 minimal.

Optionally, the moving path of the coupled magnets 21 and 22 may be limited by one or more guides.

The oscillating motion of the one or more magnets may be coupled to a mechanical system as illustrated in the examples that follow.

Figure 3:
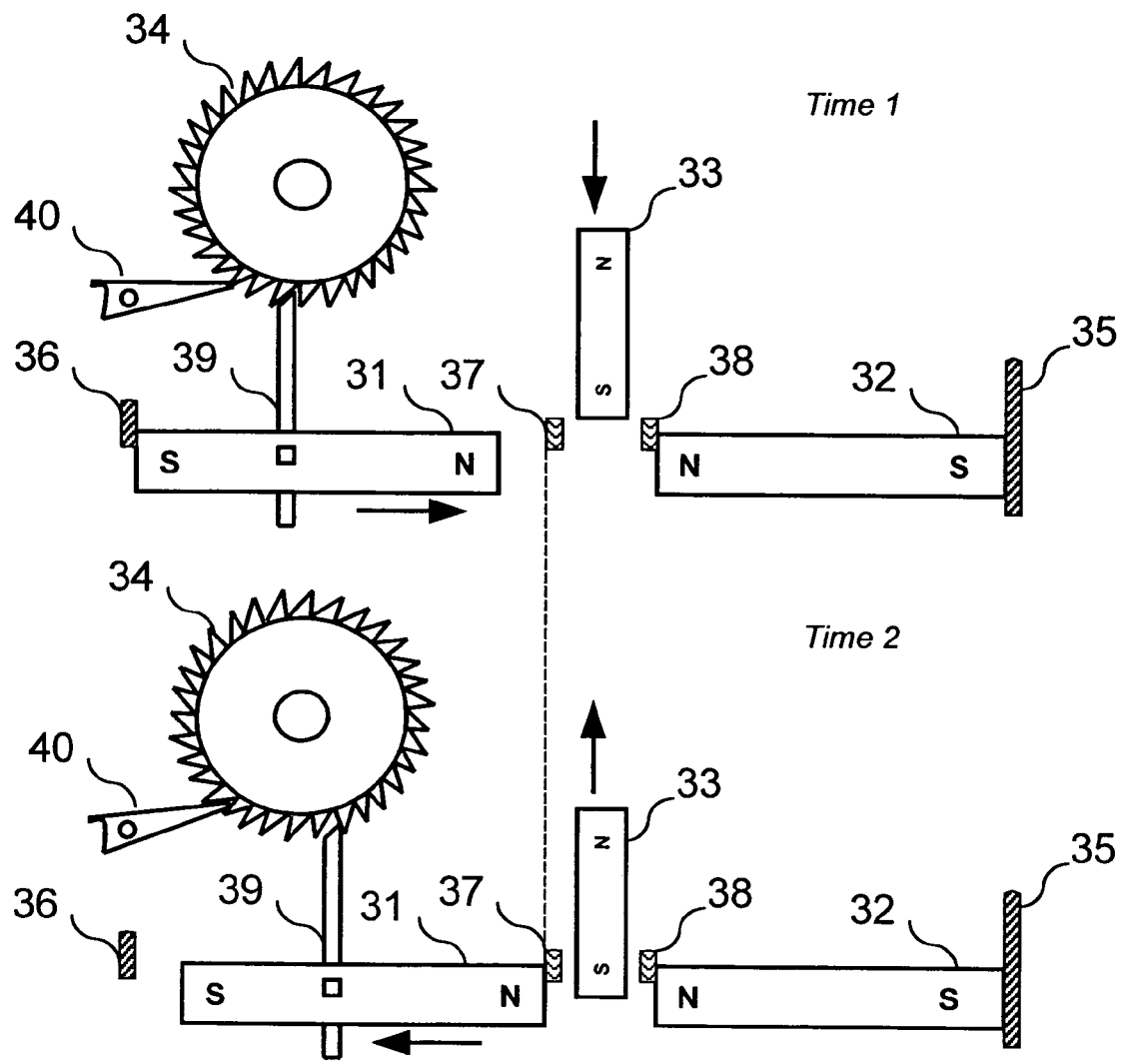
FIG. 3 is a schematic diagram illustrating a gear magnetic drive with one ratchet according to another embodiment of the invention.

Generally, at least one of the moveable or oscillating magnets may be coupled to a gear or ratchet. FIG. 3 is a schematic, pictorial diagram illustrating an example of a mechanical system wherein the magnet motion is coupled to a gear. The magnet motion occurs between two states (at time 1 and time 2) of a given cycle, either of which may precede the other. The mechanical system includes two magnets 31 and 32, a magnetic field modifier 33, and a gear 34. In a first time period, the two repelling magnets 31 and 32 are presented with the magnetic field modifier 33 located in a first position. A subsequent time period of the cycle is presented at time 2 in FIG. 3, which is referred to as a second time period. In the second time period, a certain means is used to drive the magnetic field modifier 33 in the repelling magnetic field between the coupled magnets 31 and 32. As in the switch embodiments described above, the magnetic field modifier 33 alters the repelling magnetic field between the coupled magnets 31 and 32 such that two attractive fields are produced and the coupled magnets 31 and 32 move relatively toward each other. In the example of FIG. 3, the magnet 32 is fixed by a mechanical stop 38 allowing the entire throw distance to be performed by the magnet 31 that is attached to the gear 34. Fixing the position of the coupled magnet 32 that is not driving the gear allows the throw distance of the non-fixed magnet 31 reach its maximum. The attachment in this example is a pawl or pivot arm 39. The motion of the magnet 31 moves the gear one notch per cycle. An anti-rotation stop 40 is used to keep the gear at its new position. The entire cycle may be repeated to drive the gear 34. It is clear to those in the mechanical arts that simple modifications may be made to drive the gear clockwise or counter-clockwise.

The mechanical stops 37 and 38 should be placed in such a manner that they may not interfere with the magnetic field between the coupled magnets 31 and 32. Preferably, the mechanical stops 37 and 38 are placed adjacent to the outer edge of the coupled magnets 31 and 32 so that the magnetic field impact of the mechanical stops relative to the magnetic field modifier 33 is relatively small.

Optionally, the moving path of the coupled magnets 31 and 32 may be limited by one or more guides.

The variables for the switch system described above also apply to the gear systems. For example, the size of the magnets, the polarity of the magnets, the use of a magnet or non-magnet as a field modifier, and the alignment of the coupled magnets relative to the field modifier may all be varied without diverging from the general concept of the invention.

Figure 4:
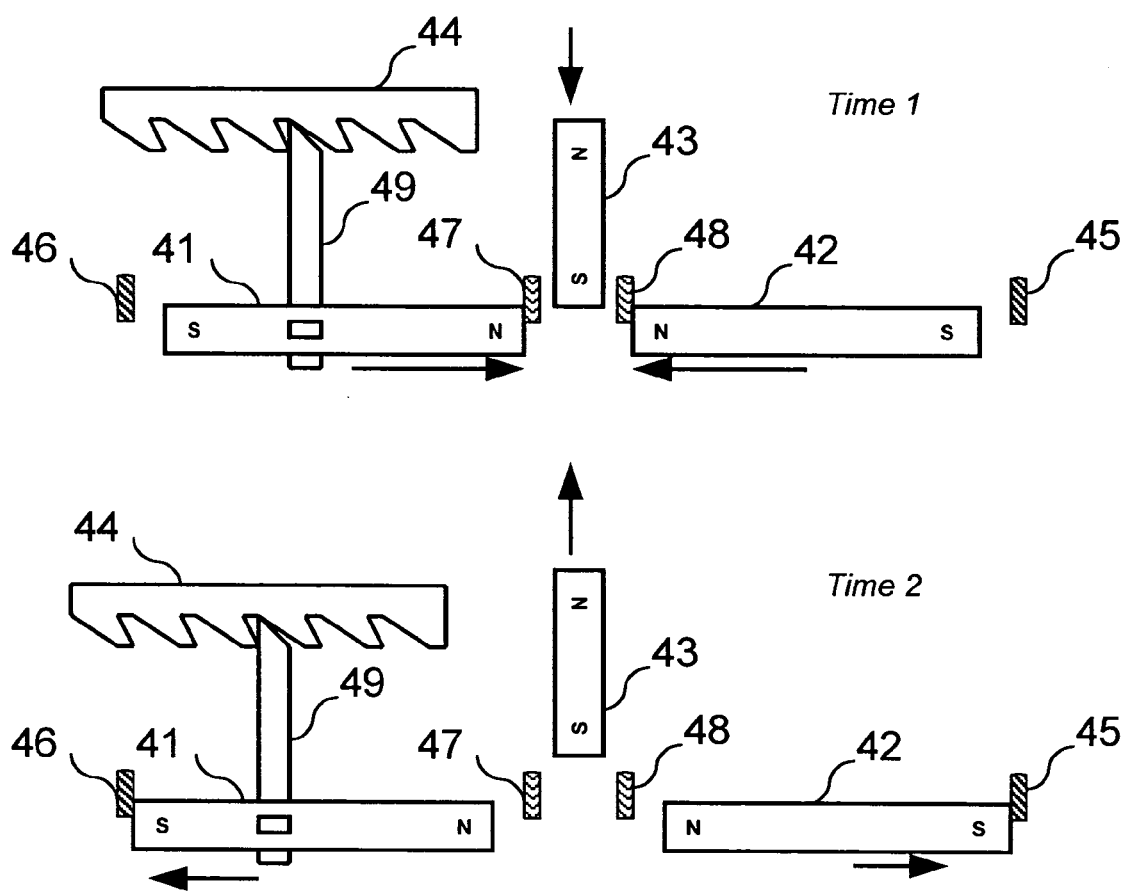
FIG. 4 is a schematic diagram illustrating a linear magnetic drive according to another embodiment of the invention.

FIG. 4 is a schematic, pictorial diagram illustrating an oscillating magnetic drive coupled to a linear ratchet or rack. Two time periods (time 1 and time 2) of a given cycle are presented, either of which may precede the other. The magnetic drive includes two magnets 41 and 42, a field modifier 43, and a linear ratchet 44 attached to magnet 41 via pawl 49. In the first given period of time (time 1), two repelling magnets 41 and 42 are presented with the field modifier 43 located in a first position. A certain means is used to drive the field modifier 43 in the magnetic field between the coupled magnets 41 and 42. The magnetic field modifier 43 alters the repelling magnetic field between the coupled magnets 41 and 42 into an attracting magnetic field between the magnet 41 and the modifier 43 and an attracting magnetic field between the magnet 42 and the modifier 43, which attract the magnets 41 and 42 to move toward each other until they reach the mechanical stops 47 and 48.

The mechanical stops 47 and 48 should be placed in such a manner that they may not interfere with the magnetic field between the coupled magnets 41 and 42. Preferably, the mechanical stops 47 and 48 are placed adjacent to the outer edge of the coupled magnets 41 and 42 so that the magnetic field impact of the mechanical stops relative to the magnetic field modifier 43 is minimized.

Optionally, the moving path of the coupled magnets 41 and 42 may be limited by one or more guides.

Alternatively, two attracting magnets may be used for a switch system as illustrated in FIG. 2.

In the second time period (time 2), a certain means is used to remove the field modifier 43 from the magnetic field between the coupled magnets 41 and 42. The repelling force between the coupled magnets 41 and 42 drives them apart until they reach the stops 45 and 46. As in any of the previously described embodiments, a mechanical or electromechanical means known to those skilled in the art may be used to drive the magnetic field modifier 43 in or out.

Alternatively, magnet 42 can be fixed in position. This allows the entire throw distance to be performed by the magnet 41 that is attached to the linear ratchet drive 44 via the pawl 49. Fixing the position of the coupled magnet 42 that is not driving the ratchet or rack allows the throw distance of the non-fixed magnet 41 to reach its maximum. Common means can be used to hold the linear drive 44 in position such that each step of the movable magnet results in the drive being driven in a given direction. In addition, common mechanisms can be used to return the drive to a starting location. In this example, the motion of the magnet 41 moves the linear ratchet 44 one notch per cycle. The stop 47 is used to keep the drive at its new position. The entire cycle may be repeated to drive the linear ratchet. It is clear to those in the mechanical arts that simple modifications may be made to drive the linear drive relative to the coupled magnets in one direction or the other.

Figure 5A:
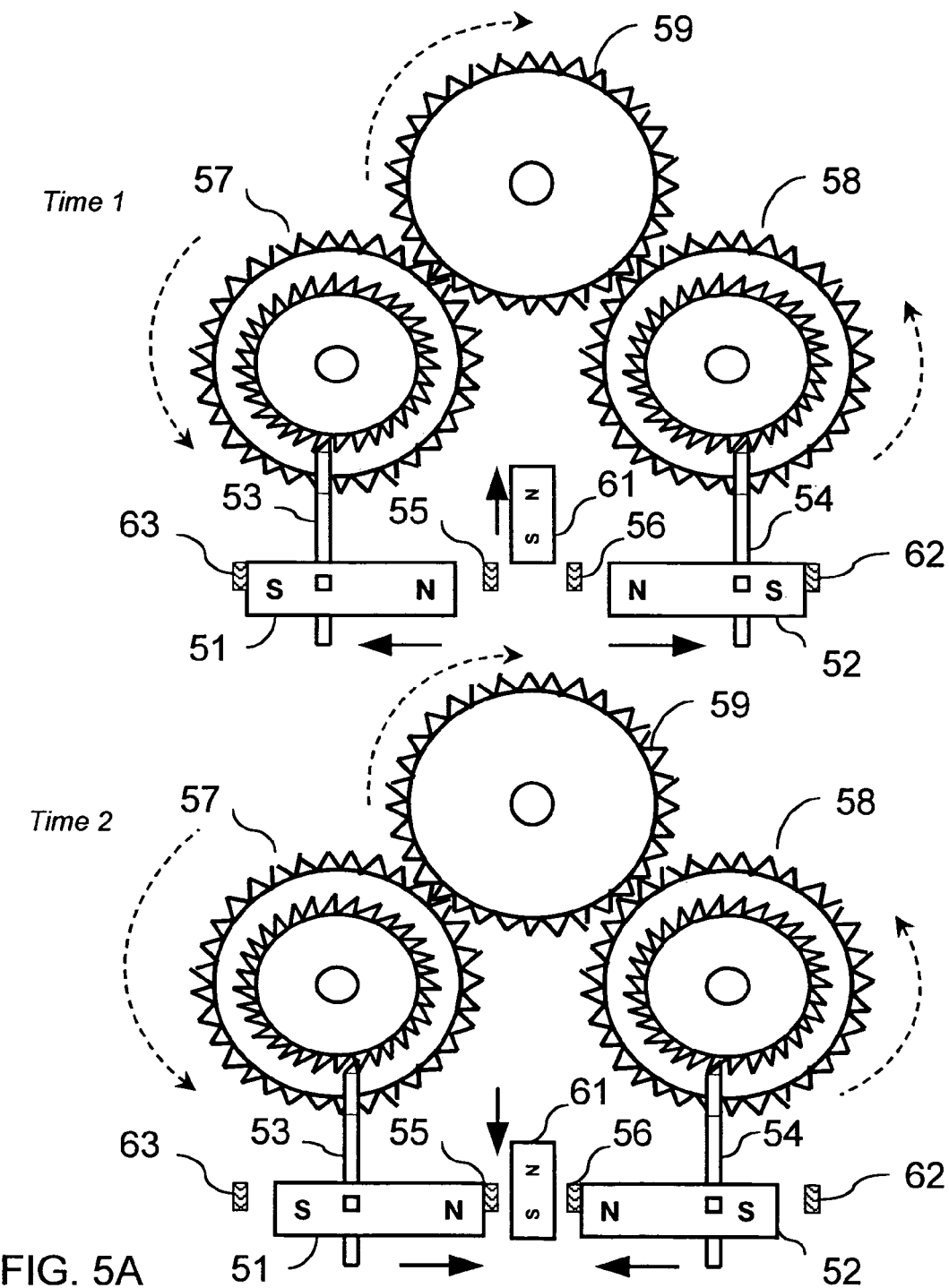
FIG. 5A is a schematic diagram illustrating a magnetic drive with two concurrently engaged ratchets according to another embodiment of the invention.

FIG. 5A is a schematic, pictorial diagram illustrating two states of a single-direction magnetic drive according to another preferred embodiment of this invention. In the illustrated example, each of the coupled magnets 51 and 52 is connected to its own ratchet, i.e. ratchet 53 or ratchet 54, which is in turn connected to its own gear, i.e. gear 57 or gear 58. Gear 57 and gear 58 are mechanically coupled to gear 59 that may be connected to a screw or other mechanical device. A cycle of operation includes moving a magnetic field modifier 61 into, and removing it from, the magnetic field between the magnets 51 and 52. Before the magnetic field modifier 61 is inserted, the repelling magnetic field keeps the coupled magnets 51 and 52 apart from each other until they reach the mechanical stops 62 and 63. When the magnetic field modifier 61 is moved into the repelling magnetic field between the coupled magnets 51 and 52, the magnetic field between the magnet 51 and the modifier 61 and the magnetic field between the modifier 61 and the magnet 52 are enhanced. When the magnetic field modifier 61 reaches a critical point, the attracting force caused by these two attracting magnetic fields overcomes the repelling force caused by the original repelling magnetic field between the coupled magnets 51 and 52, thus results in displacements of the magnets 51 and 52, which are used to drive gear 59 via the ratchets. When the coupled magnets 51 and 52 move toward each other until they reach the mechanical stops 55 and 56, the ratchet 53 turns the gear 57 one notch. While the modifier 61 is removed from the critical point, the magnets 51 and 52 move apart from each other until they reach the stops 62 and 63, and at this period of time, the ratchet 54 turns the gear 58 one notch. In this manner, gear 59 turns in one direction no matter the magnetic field modifier is removed from, or moved into, the magnetic field between the coupled magnets 51 and 52.

As in the embodiment illustrated in FIG. 4, an anti-rotation mechanism is used to prevent gear 57 and gear 58 from turning back. In addition, the mechanical stops 55 and 56 should be placed in such a manner that they may not interfere with the magnetic field between the coupled magnets 51 and 52. Preferably, the mechanical stops 55 and 56 are placed adjacent to the outer edge of the coupled magnets 51 and 52. Optionally, the moving path of the coupled magnets 51 and 52 may be limited by one or more guides.

Figure 5B:
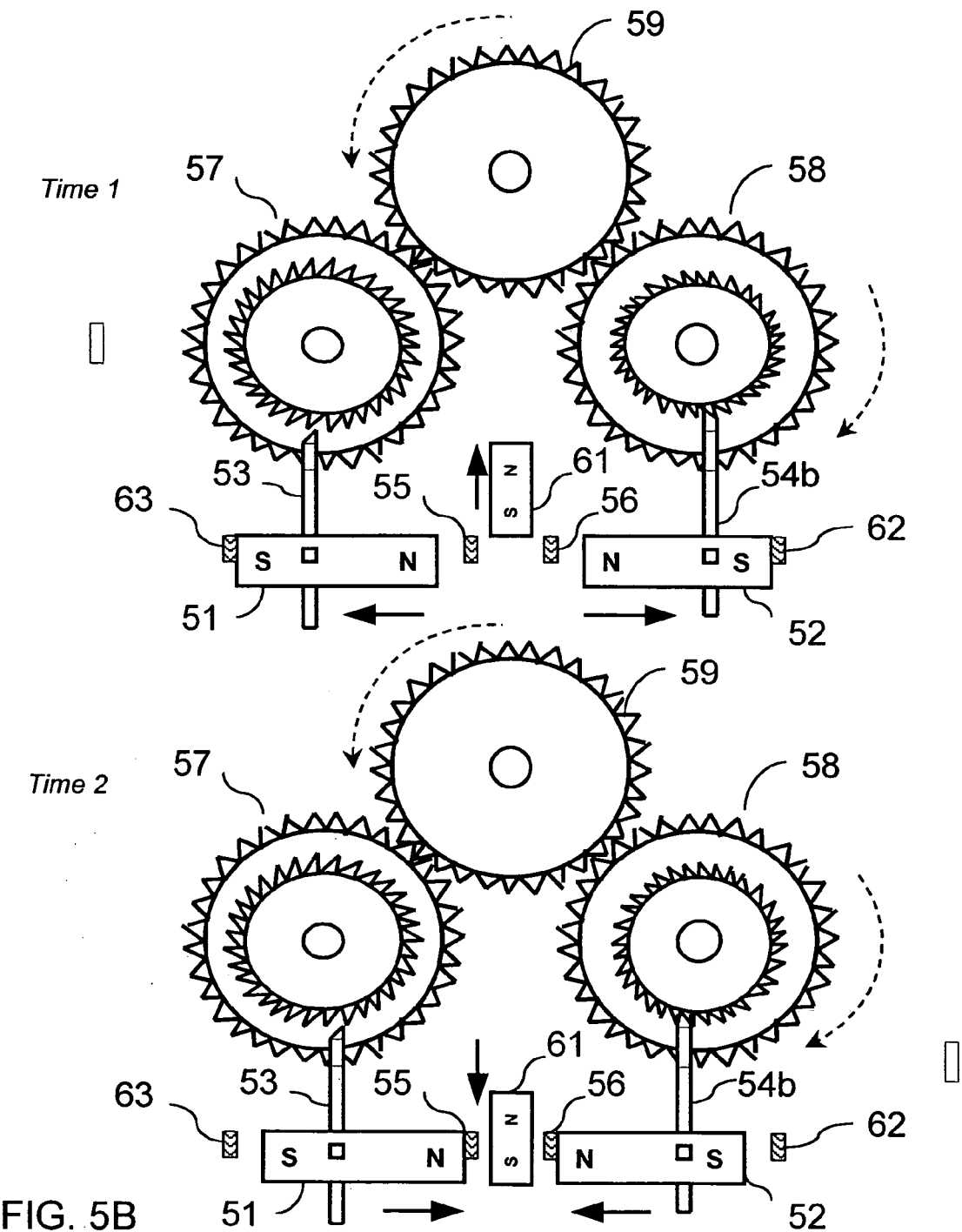
FIG. 5B is a schematic diagram illustrating a magnetic drive with two ratchets which are alternatively engaged according to another embodiment of the invention.

FIG. 5B is a schematic, pictorial diagram illustrating two states of a two-way magnetic drive according to another preferred embodiment of this invention. In the illustrated example, the ratchets 53 and 54*b* cannot be engaged concurrently because they turn gear 59 in different directions. Rather, they must be engaged alternatively. For example, when ratchet 53 is engaged, gear 59 turns clockwise, and when ratchet 54*b* is engaged, gear 59 turns counter-clockwise.

One application of the drive as illustrated in FIG. 5B is that gear 59 is connected to a screw, which may further drive another mechanical device. By a selection, possibly manual, of which ratchet is being engaged, the screw connected to gear 59 may be advanced or returned. Optionally, the screw may be used to advance, deliver, or withdraw a fluid from an associated tube or well. Those skilled in the art will recognize that the driving motion of the magnets may drive a broad range of gear mechanisms that may in-turn be connected to a larger device. Notably, any of the moving magnets of the above described embodiments may be used as a drive. Another use of the movement of the magnets would be as a pump.

In any of the drive embodiments herein, one or both of the coupled magnets may be shaped in a fashion similar to a pawl. This eliminates the use of a pawl. The movement of the magnet itself could be transferred directly to move a ratchet, drive, or gear. This would further reduce spatial requirements and may reduce cost.

Several benefits of the invention are apparent. First, in the first preferred embodiment as illustrated in FIG. 1 the energy required to insert the magnetic field modifier between the coupled magnets and hence to drive a mechanism is less than that required to drive the same mechanism directly. Naturally, the reduction in energy is dependent upon the size of the magnets, the initial distance between the magnets, and the final distance between the magnets.

Another benefit is the reduction and/or movement of spatial constraints. The smaller force required to bring the coupled magnets together necessitates a smaller mechanical device.

In addition, the positioning of the mechanical driver may be different than that used to force the coupled magnets together or to drive the mechanism directly.

The use of the magneto-mechanical drive system connected to a gear or a pump disclosed herein is limited only to the global use of gear based systems. In addition, the magneto-mechanical system described herein can be used to drive a pump or an air pressure based system. For example, the magneto-mechanical drive system may be used to pump a fluid.

One application is the delivery of a fluid. A one-way drive or screw based system such as that of FIG. 3 or FIG. 5A may be used to deliver a fluid. However, a two-way drive or screw based delivery system such as that presented in FIG. 5B may be used to either advance or withdraw a fluid.

Figure 6:
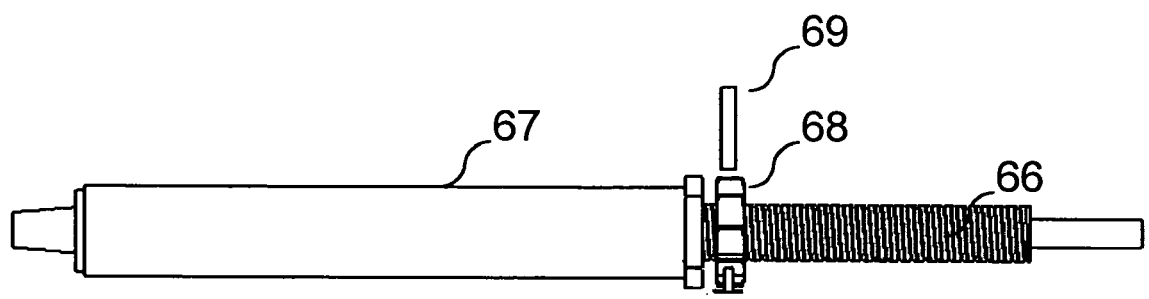
FIG. 6 is a schematic diagram illustrating the controlled release of potential energy to drive a fluid according to the invention.

In one deployment of the invention, a ratchet is used to control the release of potential energy. For example, FIG. 6 presents a compression spring 66 connected to a plunger 67 that is driven by a ratchet 68. The compression spring 66 may be replaced with other sources of stored potential energy such as a compressed gas. The plunger 67 may be part of a mechanism for delivery of a fluid. The ratchet 68 may be stepped by a magneto-mechanical drive system, as described herein. For example, a cyclic movement of a magnetic field modifier 69 induces the movement of the ratchet 68, which allows the potential energy of the spring 66 to be released in a controlled manner. An alternative mechanism may be escapement. This system has several benefits including requiring less energy in driving the ratchet 68 of the fluid delivery system, a force supplied by the potential energy to prevent the backflow of a fluid, and a steady, accurate, precise, or reproducible flow.

In a noninvasive glucose analyzer, a fluid may be applied between the sampling site and the incident or collection optics. The fluid may have one or more of a number of parameters including refractive index matching, optical coupling, air gap displacement, temperature modification, as well as temperature stabilization. More specifically, an optic may be coupled to a sample with a coupling fluid such as Fluorinert™, a fluorocarbon, a fluorocarbon polymer, a fluorocarbon mixture, FC-40, a chlorofluorocarbon, a chlorofluorocarbon mixture, Fluorolube™, glycerol, or coupling fluids as known in the noninvasive glucose determination art like those taught or reviewed in U.S. Pat. No. 6,152,876 to Robinson et al that is incorporated herein in it entirety by this reference thereto. It may be desirable to heat or replace the fluid as a function of time. General discussions of noninvasive glucose analyzers are presented in U.S. Pat. No. 6,040,578 to Malin et al and U.S. provisional patent application No. 60/448,840 filed on Feb. 19, 2003, the content of which is incorporated herein in its entirety by this reference thereto.

Another application is the delivery of a drug in the form of a fluid. A digital mechanism of the drive coupled to a mechanical system allows for a precise and known amount of a fluid, such as insulin, to be delivered. The compact arrangement of the driving force allows for a miniaturized insulin delivery system to make pre-defined deliveries. In addition, the small force required for modifying the magnetic field and hence for driving the associated mechanical system allows for a miniaturized and/or low power power-supply to be utilized.

In addition, the magneto-mechanical system may be used as a switch. The switch may be either mechanical or electrical. As the switch is powered by the movement of the magnetic field modifier, a separate electrical power supply to activate the system is not required. For example, the expansion or contraction of a bladder may be coupled to the magnetic field modifier in a fashion that does not require external electrical power. Such a system can also be used as an alarm where pressure differences are to be noted. One example is in the sensor of a water supply for a sprinkler system. If the sprinklers turn on, the pressure change would cause the magnetic field modifier to move resulting in a contact. This contact can close a circuit. An alarm may be associated with the closed circuit. One benefit of this system is that electrical power needs not be supplied to move the magnetic field modifier. Thus, the system could operate under a power failure.

In view of the different possible embodiments to which the principle of this invention may be applied, it should be recognized that the preferred embodiments described herein with respect to the drawings are meant to be illustrative only and should not be taken as limiting the scope of the invention. One skilled in the art will readily appreciate that other applications may be substituted for those set forth herein without departing from the spirit and scope of the present invention.

Accordingly, the invention should only be limited by the Claims included below.

What is claimed is:

1. A magnetic-mechanical apparatus, comprising:
   a pair of magnets coupled by a magnetic field and separated by a distance;
   a magnetic field modifier;
   wherein said magnetic field modifier is movable between a first location and a second location; wherein said second location is between said pair of magnets; wherein said magnetic field between said pair of magnets is altered, resulting in displacement of at least one of said pair of magnets from a first position to a second position; and
   wherein said displacement of at least one of said pair of magnets is used as a driving source.

2. The apparatus of claim 1, wherein said pair of magnets includes any of:
   permanent magnets; and
   electromagnets.

3. The apparatus of claim 1, wherein said pair of magnets are aligned having either common magnetic poles facing each other, or opposite magnetic poles facing each other.

4. The apparatus of claim 1, wherein at least one of said magnets is positionally limited to either said first position or said second position by the use of a stop.

5. The apparatus of claim 1, wherein said magnetic field modifier includes any of:
   a magnetizable material;
   a permanent magnet; and
   an electromagnet.

6. The apparatus of claim 1, wherein said mechanical apparatus comprises either a switch or a drive.

7. The apparatus of claim 1, wherein said magnetic field modifier is alternately moved from said first location to said second location such that said displacement of at least one of said magnets alternates between said first position and said second position.

8. The apparatus of claim 7, wherein said displacement is mechanically coupled to drive at least one of:
   a driving member;
   a ratchet;
   a gear; and
   a drive.

9. The apparatus of claim 8, wherein said driving member is mechanically coupled to drive at least one of:
   said ratchet;
   said gear; and
   said drive.

10. The apparatus of claim 1, wherein said displacement is physically limited by a guide.

11. The apparatus of claim 9, wherein said gear is coupled to a fluid delivery system.

12. The apparatus of claim 11, wherein said fluid delivery system is used to deliver any of:
    a coupling agent; and
    a drug.

13. The apparatus of claim 12, wherein said coupling agent comprises any of:
    a fluorocarbon;
    a chlorofluorcarbon; and
    a fluid having minimal near-infrared absorbance.

14. The apparatus of claim 11, further comprising:
    a potential energy source connected to said fluid delivery system.

15. The apparatus of claim 14, wherein said potential energy source comprises at least one of:
    a spring; and
    a compressed gas.

16. A magnetic-mechanical apparatus, comprising:
    a pair of magnets separated by a distance;
    a magnetic field modifier; and
    a first stop;
    wherein said magnetic field modifier is movable between a first location and a second location; wherein said second location is between said pair of magnets, resulting in modification of a magnetic field between said pair of magnets;
    wherein said modified magnetic field displaces at least one of said pair of magnets from a first position to a second position; and
    wherein said displacement of at least one of said pair of magnets is physically limited by said first stop.

17. The apparatus of claim 16, wherein said pair of magnets comprise any of:
    permanent magnets; and
    electromagnets.

18. The apparatus of claim 16, wherein said pair of magnets are aligned having any of:
   common magnetic poles facing each other; and
   opposite magnetic poles facing each other.

19. The apparatus of claim 16, wherein said magnetic field modifier comprise any of:
   a magnetizable material;
   a permanent magnet; and
   an electromagnet.

20. The apparatus of claim 16, further comprising a switch.

21. The apparatus of claim 20, wherein said at least one of said pair of magnets activates said switch by said displacement.

22. The apparatus of claim 16, further comprising:
   a second stop.

23. The apparatus of claim 22, wherein said magnetic field modifier is cyclically moved between said first location and said second location to cyclically alter said magnetic field between a first state and a second state;
   wherein said altered magnetic field displaces at least one of said pair of magnets to cyclically move between said first position and said second position; and
   wherein said second position of said at least one of said pair of magnets is physically limited by said second stop.

24. The apparatus of claim 23, further comprising at least one of:
   a pawl;
   a ratchet;
   a gear; and
   a drive.

25. The apparatus of claim 24, wherein said at least one of said pair of magnets is operatively connected to said pawl.

26. The apparatus of claim 25, wherein said pawl is used to drive at least one of:
   said ratchet;
   said gear; and
   said drive.

27. The apparatus of claim 26, further comprising a fluid delivery system.

28. The apparatus of claim 27, wherein said fluid delivery system is powered by at least one of:
   said gear; and
   said drive.

29. The apparatus of claim 28, wherein said fluid delivery system is used to deliver at least one of:
   a fluorocarbon;
   a chlorofluorocarbon; and
   a coupling fluid.

30. The apparatus of claim 29, wherein said coupling fluid has minimal absorption in the near-infrared spectrum.

31. A method of using a magneto-mechanical apparatus, comprising steps of:
   providing a pair of magnets separated by a distance;
   providing a magnetic field modifier;
   moving said magnetic field modifier between a first position and a second position; wherein said second position is between said pair of magnets; wherein a magnetic field between said pair of magnets is altered between a first state and a second state;
   wherein said altered magnetic field displaces at least one of said pair of magnets between a first location and a second location; and
   using said displacement of said at least one of said pair of magnets.

32. The method of claim 31, wherein said pair of magnets comprise any of:
   permanent magnets; and
   electromagnets.

33. The method of claim 31, wherein said magnetic field modifier comprises any of:
   a magnetizable material;
   a permanent magnet; and
   an electromagnet.

34. The method of claim 31, wherein said step of using said displacement activates at least one of:
   a switch; and
   an electrical contact.

35. The method of claim 31, wherein said step of moving said magnetic field modifier further comprises the step of:
   alternating a position of said magnetic field modifier between said first position and said second position to alternate said magnetic field between said pair of magnets between said first state and said second state;
   wherein at least one of said pair of magnets alternates between said first location and said second location.

36. The method of claim 35, wherein at least one of said pair of magnets is mechanically coupled to at least one of:
   a pawl;
   a ratchet;
   a gear; and
   a drive.

37. The method of claim 36, wherein said step of using said displacement comprises driving at least one of:
   said ratchet;
   said gear; and
   said drive.

38. The method of claim 36, wherein said pawl is mechanically attached to said at least one of said pair of magnets.

39. The method of claim 38, wherein said step of using said displacement comprises driving via said pawl at least one of:
   said ratchet;
   said gear; and
   said drive.

40. The method of claim 39, wherein any of said ratchet, said gear, and said drive drives a fluid delivery system.

41. The method of claim 40, wherein said fluid delivery system delivers any of:
   a coupling fluid; and
   a drug.

42. The method of claim 41, wherein said coupling fluid comprises any of:
   a fluorocarbon;
   a chlorofluorocarbon; and
   a fluid that enhances photon transport between a first medium and a second medium.

43. A method of using a magneto-mechanical apparatus, comprising steps of:
   providing a pair of magnets separated by a distance having a magnetic field between said pair of magnets;
   providing a magnetic field modifier;
   cycling said magnetic field modifier between a first position and a second position, wherein said second position is between said pair of magnets, wherein said magnetic field alternates between a first state and a second state, and said first state and said second state result in cycling at least one of said pair of magnets between a first location and a second location.

44. The method of claim 43, wherein at least one of said pair of magnets is coupled to a drive member.

45. The method of claim 44, wherein said step of cycling at least one of said pair of magnets results in repeatably moving said drive member.

46. The method of claim 45, wherein said step of repeatably moving said drive member results in repeatably moving any of:
   a ratchet;
   a gear; and
   a drive.

47. The method of claim 46, wherein at least one of said pair of magnets is coupled to a fluid delivery system, said fluid delivery system being driven by at least one of said ratchet, said gear, and said drive.

48. An apparatus comprising:
   a pair of magnet members being spaced apart from each other; and
   a third member as a magnetic field modifier;
   wherein when said third member is moved to a critical position relative to said pair of magnet members by either moving into or departing from a magnetic field between said pair of magnets, said magnetic field therebetween is altered to such an extent that at least one of said pair of magnet members is displaced between a first position and a second position;
   wherein when said third member is removed from said critical position, a magnetic field therebetween is altered such that said at least one of said pair of magnet members returns to said first position; and
   wherein said third member is cyclically moved to and removed from said critical position to cyclically alter said magnetic field to induce cyclic movement of said at least one of said pair of magnet members between said first and second positions.

49. The apparatus of claim 48, wherein any of said pair of magnet members can be any of:
   a permanent magnet; and
   an electromagnet.

50. The apparatus of claim 48, wherein said pair of magnet members have like poles facing to each other.

51. The, apparatus of claim 50, wherein said first position is maintained by the repelling force between said pair of magnet members against a first fixed stop, and wherein said second position is maintained by the attracting force between said third member and said at least one of said pair of magnet members against a second fixed stop placed between said third member and said at least one of said pair of magnet members.

52. The apparatus of claim 48, wherein said pair of magnet members have opposite poles facing to each other.

53. The apparatus of claim 52, wherein said first position is maintained by a pulling force of an elastic member attaching said at least one of said pair of magnet members to a first fixed stop, and wherein said second position is maintained by an attracting force between said third member and said at least one of said pair of magnet members against a second fixed stop placed between said third member and said at least one of said pair of magnet members.

54. The apparatus of claim 48, wherein said third member can be any of:
   a permanent magnet;
   an electromagnet; and
   a piece of magnetizable metal.

55. The apparatus of claim 48, wherein said displaced at least one of said pair of magnet members is coupled to a switch.

56. The apparatus of claim 48, wherein said displaced at least one of said pair of magnet members is coupled to a drive.

57. The apparatus of claim 56, wherein said drive is a linear ratchet.

58. The apparatus of claim 56, wherein said drive is a circular ratchet.

59. A magneto-mechanical switch, comprising:
   a pair of magnet members having like poles facing to each other in a first position in which a repelling force between said pair of magnet members supports each of said pair of magnet members against a fixed stop; and
   a third member comprising a magnetic field modifier;
   wherein when said third member is moved to a critical position relative to said pair of magnet members, a magnetic field therebetween is altered to such an extent that said pair of magnet members are moved between said first position and a second position, said second position being maintained by an attracting force between said third member and each of said pair of magnet members against a fixed stop placed between said third member and each of said pair of magnet members;
   wherein when said third member is removed from said critical position, said pair of magnet members return from said second position to said first position; and
   wherein said third member is cyclically moved to and removed from said critical position said magnetic field is cyclically altered and induces cyclic movement between said pair of magnet members between said first and second positions.

60. A magneto-mechanical switch, comprising:
   a pair of magnet members having opposite poles facing each other in a first position, wherein each of said pair of magnet members is pulled by an elastic member attached to a fixed stop to space said pair of magnet members apart from each other; and
   a third member comprising a magnetic field modifier;
   wherein when said third member is moved to a critical position relative to said pair of magnet members, a magnetic field therebetween is altered to such an extent that said pair of magnet members are moved between said first position and a second position, said second position being maintained by an attracting force between said third member and each of said pair of magnet members against a fixed stop placed between said third member and each of said pair of magnet members;
   wherein when said third member is removed from said critical position, said pair of magnet members return from said second position to said first position; and
   wherein said third member is cyclically moved to and removed from said critical position said magnetic field is cyclically altered and induces cyclic movement between said pair of magnet members between said first and second positions.

61. A magneto-mechanical drive, comprising:
   a pair of magnet members having like poles facing each other, a first of which is fixed in position and a second of which is in a first position in which a repelling force between said pair of magnet members supports said second magnet member against a fixed stop, said second magnet member being coupled to a gear; and
   a third member comprising a magnetic field modifier;
   wherein when said third member is moved to a critical position relative to said pair of magnet members, a magnetic field therebetween is altered to such an extent that said second magnet member moves between said first position and a second positions said second position being maintained by attracting forces between said third member and each of said pair of magnet members against a fixed stop placed between said third member and said second magnet members;

wherein when said third member is removed from said critical position, said second magnet member returns from said second position to said first position;

wherein said third member is cyclically moved to and removed from said critical position said magnetic field is cyclically altered and induces cyclic movement between said second magnet member said first and second positions; and wherein each cycle of operation of said third member approaching to and departing from said critical position moves said gear at least one notch.

* * * * *